United States Patent
Kobayashi

(10) Patent No.: US 10,548,493 B2
(45) Date of Patent: Feb. 4, 2020

(54) BIOLOGICAL INFORMATION MEASUREMENT SYSTEM

(71) Applicant: Nihon Kohden Corporation, Tokyo (JP)

(72) Inventor: Naoki Kobayashi, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 770 days.

(21) Appl. No.: 15/082,813

(22) Filed: Mar. 28, 2016

(65) Prior Publication Data

US 2016/0287099 A1 Oct. 6, 2016

(30) Foreign Application Priority Data

Mar. 30, 2015 (JP) .................................. 2015-069911

(51) Int. Cl.
*A61B 5/026* (2006.01)
*A61B 5/024* (2006.01)
*A61B 5/1455* (2006.01)

(52) U.S. Cl.
CPC ........ *A61B 5/0261* (2013.01); *A61B 5/02422* (2013.01); *A61B 5/14551* (2013.01);
(Continued)

(58) Field of Classification Search
CPC .... A61M 2205/3313; A61M 2230/205; A61B 5/0261; A61B 5/14551; A61B 5/02422; A61B 5/7271; A61B 5/7282
See application file for complete search history.

(56) References Cited

U.S. PATENT DOCUMENTS

| 4,869,253 A | * | 9/1989 | Craig, Jr. ........... A61B 5/14551 |
| | | | 600/323 |
| 5,697,371 A | | 12/1997 | Aoyagi et al. |

(Continued)

FOREIGN PATENT DOCUMENTS

| JP | 53-26437 | 8/1978 |
| JP | H01500647 A | 9/1989 |

(Continued)

OTHER PUBLICATIONS

"Pulse Oximetry—Wikipedia", obtained on Mar. 28, 2016 from https://en.wikipedia.org/wiki/Pulse_oximetry.
(Continued)

*Primary Examiner* — Eric F Winakur
*Assistant Examiner* — Abid A Mustansir
(74) *Attorney, Agent, or Firm* — Dorsey & Whitney LLP

(57) ABSTRACT

A light emitting unit emits first light and second light having different wavelengths. A photoreception unit outputs first and second signals depending on photoreception intensities of the first and second light transmitted through or reflected by biological tissue. A processing period setting unit extracts a signal cycle corresponding to the cardiac cycle for the first or second signal and sets a processing period in a first part dominantly affected by arterial blood flowing to the tissue or a second part dominantly affected by venous blood flowing from the tissue in the signal cycle. First and second change amount acquisition units obtain first and second change amounts corresponding to the attenuation change amounts of the first and second light from the first and second signals in the processing period. A concentration calculation unit calculates the concentration of light absorbing substance in blood from the first and second change amounts.

20 Claims, 11 Drawing Sheets

(52) U.S. Cl.
CPC ............... *A61M 2205/3313* (2013.01); *A61M 2230/205* (2013.01)

(56) References Cited

U.S. PATENT DOCUMENTS

| | | | |
|---|---|---|---|
| 5,999,841 A * | 12/1999 | Aoyagi | A61B 5/0275 600/431 |
| 7,376,452 B2 | 5/2008 | Kobayashi et al. | |
| 8,024,021 B2 | 9/2011 | Aoyagi et al. | |
| 8,406,838 B2 | 3/2013 | Kato | |
| 2003/0189492 A1* | 10/2003 | Harvie | A61M 16/0051 340/573.1 |
| 2004/0176670 A1 | 9/2004 | Takamura et al. | |
| 2005/0256386 A1* | 11/2005 | Chan | A61B 5/14551 600/335 |
| 2008/0262327 A1 | 10/2008 | Kato | |
| 2011/0082357 A1 | 4/2011 | Hornick | |
| 2011/0158914 A1 | 6/2011 | Yamada | |
| 2014/0371557 A1 | 12/2014 | Kobayashi et al. | |
| 2016/0106325 A1* | 4/2016 | Kang | A61B 5/0261 600/480 |

FOREIGN PATENT DOCUMENTS

| | | |
|---|---|---|
| JP | H07155312 A | 6/1995 |
| JP | H07222723 A | 8/1995 |
| JP | 2001078990 A | 3/2001 |
| JP | 2004230000 A | 8/2004 |
| JP | 2006231012 A | 9/2006 |
| JP | 2009279384 A | 12/2009 |
| JP | 2011082357 A | 4/2011 |
| JP | 2011131002 A | 7/2011 |
| JP | 2015000127 A | 1/2015 |
| WO | 2006009178 A1 | 1/2006 |

OTHER PUBLICATIONS

English Translation of First Office Action dated Nov. 27, 2018 for Japanese application No. 2015-069911.
English Translation of Notice of Reasons for Refusal dated Jun. 27, 2019 received in JP Application No. 2015-069911.
English translation of Notice of Reasons for Refusal for JP Application No. 2015-069911, dated Nov. 19, 2019.

* cited by examiner

TIME (SECOND)

R = 0.7771

LOGARITHMIC VALUE OF I1

BIOLOGICAL INFORMATION MEASUREMENT SYSTEM

CROSS-REFERENCE TO RELATED APPLICATION(S)

This application claims priority to and the benefit under 35 U.S.C. § 119(a) of the earlier filing date of Japanese Patent Application No. 2015-069911 filed Mar. 30, 2015, the disclosure of which is hereby incorporated by reference, in its entirety, for any purpose.

BACKGROUND

Examples of the present invention relate to a system measuring biological information.

A pulse photometer is known as an example of an apparatus constituting such a biological information measurement system. A pulse photometer is an apparatus for calculating the concentration of a light absorbing substance in blood of a subject. Specifically, light having a plurality of wavelengths illuminates the biological tissue of the subject. The plurality of wavelengths are determined so that the ratio of the absorption coefficients of blood differs depending on the concentration of the light absorbing substance in blood. The amount of light having each wavelength transmitted through or reflected by the biological tissue is detected. The light amount of each wavelength depends on the pulsation of the blood of the subject. Accordingly, the time-dependent change of the light amount of each wavelength caused by the pulsation is obtained as a pulse wave signal. The amplitude of the pulse signal of each wavelength corresponds to the attenuation change amount of the waveform. The concentration of the light absorbing substance in blood is calculated based on the ratio of the attenuation change amount of each waveform (see JP-B-53-026437, for example).

Arterial blood oxygen saturation is known as the concentration of a light absorbing substance in blood. Arterial blood oxygen saturation is the ratio of oxyhemoglobin to the amount of hemoglobin capable of carrying oxygen. That is, oxyhemoglobin is an example of a light absorbing substance in blood. Another example of a light absorbing substance in blood is a dye as an indicator to be administered to a blood flow to measure the transit time of the biological tissue.

SUMMARY

An object of the invention is to easily measure various types of biological information using the principle of a pulse photometer.

To achieve the above object, according to a first aspect of the invention, there is provided a biological information measurement system including a light emitting unit emitting first light having a first wavelength and second light having a second wavelength, a photoreception unit outputting a first signal and a second signal depending on photoreception intensity of the first light and photoreception intensity of the second light transmitted through or reflected by biological tissue of a subject, a processing period setting unit extracting a signal cycle corresponding to a cardiac cycle of the subject for one of the first signal and the second signal and setting a processing period in one of a first part in which an effect of arterial blood flowing to the biological tissue is dominant and a second part in which an effect of venous blood flowing from the biological tissue is dominant in the signal cycle, a first change amount acquisition unit acquiring a first change amount corresponding to an attenuation change amount of the first light based on the first signal in the processing period, a second change amount acquisition unit acquiring a second change amount corresponding to an attenuation change amount of the second light based on the second signal in the processing period, a concentration calculation unit calculating a concentration of a light absorbing substance in blood of the subject based on the first change amount and the second change amount, and an output unit outputting the concentration.

Examples of the light absorbing substance in blood are oxyhemoglobin, deoxyhemoglobin, a dye, and the like.

In such a structure, the signal cycle corresponding to the cardiac cycle of the subject obtained based on the signal corresponding to the photoreception intensity in the photoreception unit is divided into the part in which the effect of arterial blood flowing to the biological tissue is dominant and the part in which the effect of venous blood flowing from the biological tissue is dominant. The processing period is set in only one of these parts and the attenuation change amounts of these pieces of light having the individual wavelengths are obtained. The processing period is necessarily shorter than the diastole phase or the systole phase of the heart of the subject. That is, the concentration of a light absorbing substance in blood of the subject can be calculated at high speed while suppressing calculation loads. Accordingly, biological information can be measured easily using the principle of a pulse photometer.

The biological information measurement system according to the first aspect may further include a differential signal acquisition unit acquiring a differential signal by differentiating the one of the first signal and the second signal, in which the processing period setting unit sets the processing period in the first part based on a minimum value of the differential signal.

In such a structure, only by performing simple processing that differentiates the first signal or the second signal, the processing period can be set at the feature point at which the effect arterial blood flowing to the biological tissue is the most dominant. Accordingly, it is possible to improve the effect of the above structure that can easily measure biological information using the principle of the pulse photometer.

Alternatively, the biological information measurement system according to the first aspect may further include a differential signal acquisition unit acquiring a differential signal by differentiating the one of the first signal and the second signal, in which the processing period setting unit sets the processing period in the second part based on a maximum value of the differential signal.

In such a structure, only by performing simple processing that differentiates the first signal or the second signal, the processing period can be set at the feature point at which the effect of venous blood flowing from the biological tissue is the most dominant. Accordingly, it is possible to improve the effect of the above structure that can easily measure biological information using the principle of the pulse photometer.

To achieve the above object, according to a second aspect of the invention, there is provided a biological information measurement system including a light emitting unit emitting first light having a first wavelength and second light having a second wavelength, a photoreception unit outputting a first signal or a second signal depending on photoreception intensity of the first light and photoreception intensity of the second light transmitted through or reflected by biological tissue of a subject, a processing period setting unit extracting a signal cycle corresponding to a cardiac cycle of the subject for each of the first signal and the second signal and setting a first processing period in a first part in which an effect of arterial blood flowing to the biological tissue and setting a second processing period in a second part in which an effect of venous blood flowing from the biological tissue is dominant in the signal cycle, a first change amount acquisition unit acquiring a first change amount corresponding to an attenuation change amount of the first light in the first processing period based on the first signal in the first processing period, a second change amount acquisition unit acquiring a second change amount corresponding to an attenuation change amount of the second light in the first processing period based on the second signal in the first processing period, a first concentration calculation unit calculating a first concentration corresponding to a concentration of a light absorbing substance in blood of the subject in the first processing period based on the first change amount and the second change amount, a third change amount acquisition unit acquiring a third change amount corresponding to an attenuation change amount of the first light in the second processing period based on the first signal in the second processing period, a fourth change amount acquisition unit acquiring a fourth change amount corresponding to an attenuation change amount of the second light in the second processing period based on the second signal in the second processing period, a second concentration calculation unit calculating a second concentration corresponding to the concentration of the light absorbing substance in blood of the subject in the second processing period based on the third change amount and the fourth change amount, a transit time calculation unit calculating a transit time of blood in the biological tissue based on the first concentration and the second concentration, and, an output unit outputting at least one of the first concentration, the second concentration, and the transit time.

According to the second aspect of the invention as described above, there is provided a biological information measurement system including a light emitting unit emitting first light having a first wavelength and second light having a second wavelength, a photoreception unit outputting a first signal or a second signal depending on photoreception intensity of the first light and photoreception intensity of the second light transmitted through or reflected by biological tissue of a subject, a processing period setting unit extracting a signal cycle corresponding to a cardiac cycle of the subject for each of the first signal and the second signal and setting a first processing period in a first part in which an effect of arterial blood flowing to the biological tissue and setting a second processing period in a second part in which an effect of venous blood flowing from the biological tissue is dominant in the signal cycle, a first change amount acquisition unit acquiring a first change amount corresponding to an attenuation change amount of the first light in the first processing period based on the first signal in the first processing period, a second change amount acquisition unit acquiring a second change amount corresponding to an attenuation change amount of the second light in the first processing period based on the second signal in the first processing period, a first concentration calculation unit calculating a first concentration corresponding to a concentration of a light absorbing substance in blood of the subject in the first processing period based on the first change amount and the second change amount, a third change amount acquisition unit acquiring a third change amount corresponding to an attenuation change amount of the first light in the second processing period based on the first signal in the second processing period, a fourth change amount acquisition unit acquiring a fourth change amount corresponding to an attenuation change amount of the second light in the second processing period based on the second signal in the second processing period, a second concentration calculation unit calculating a second concentration corresponding to the concentration of the light absorbing substance in blood of the subject in the second processing period based on the third change amount and the fourth change amount, a transit time calculation unit calculating a transit time of blood in the biological tissue based on the first concentration and the second concentration, and, an output unit outputting at least one of the first concentration, the second concentration, and the transit time.

Examples of the light absorbing substance in blood are oxyhemoglobin, deoxyhemoglobin, a dye, and the like.

In such a structure, the signal cycle corresponding to the cardiac cycle of the subject obtained based on the signal corresponding to the photoreception intensity in the photoreception unit is divided into a portion in which the effect of arterial blood flowing to the biological tissue is dominant and a portion in which the effect of venous blood flowing from the biological tissue is dominant. Then, the attenuation change amount of these pieces of light having the individual wavelengths are obtained for both parts, so that two types of concentrations of a light absorbing substance in blood having different time-dependent change characteristics are obtained. This enables the calculation of the transit time of blood in the biological tissue while using the principle of a pulse photometer having no invasion. The first processing period and the second processing period are necessarily shorter than the diastole phase or systole phase of the heart of the subject. That is, the concentration of the light absorbing substance in blood and the transit time of blood of the subject can be calculated at high speed while suppressing calculation loads. Accordingly, biological information can be measured easily using the principle of a pulse photometer.

The biological information measurement system according to the second aspect may be configured such that the transit time calculation unit calculates the transit time based on a time difference between a time when the first concentration takes the maximum value and a time when the second concentration takes the maximum value.

Alternatively, the biological information measurement system according to the second aspect may be configured such that the transit time calculation unit calculates the transit time based on a time difference between a time when the first concentration exceeds a threshold and a time when the second concentration exceeds the threshold.

Alternatively, the biological information measurement system according to the second aspect may be configured such that the transit time calculation unit calculates the transit time based on a difference between a first mean transit time obtained based on time-dependent change of the first concentration and a second mean transit time obtained based on time-dependent change of the second concentration.

Alternatively, the biological information measurement system according to the second aspect may be configured such that the transit time calculation unit calculates the transit time based on a cross correlation function between the first concentration and the second concentration.

The biological information measurement system according to the second aspect may further include an air circuit supplying air to be inhaled by the subject and an oxygen concentration adjusting unit adjusting a concentration of oxygen included in the air.

In such a structure, the arterial blood oxygen saturation of blood transmitted through the biological tissue can be changed by changing the concentration of oxygen included in air to be inhaled by the subject. That is, it is possible to measure the transit time of blood in the biological tissue of the subject using the principle of a pulse photometer without the need to administer an indicator to a blood flow. Accordingly, biological information of the subject can be measured more easily using the principle of a pulse photometer.

The biological information measurement system according to the second aspect may further include a cuff attachable to the subject so as to press a part of a blood flow upstream of the biological tissue and a pressure control unit capable of controlling pressure of the cuff.

In such a structure, the arterial blood oxygen saturation of blood can be changed by stopping a blood flow through pressing with the cuff. That is, it is possible to measure the transit time of blood in the biological tissue of the subject using the principle of a pulse photometer without the need to administer an indicator to a blood flow. Accordingly, biological information of the subject can be measured more easily using the principle of a pulse photometer.

The biological information measurement system according to the second aspect may further include a notifying unit making a notice when a value of the transit time falls outside a predetermined range.

In such a structure, the notice from the notifying unit helps to determine peripheral circulation incompetence. For example, when the value of the transit time falls below a predetermined range, the disease state of sepsis can be suspected.

To achieve the above object, according to a third aspect of the invention, there is provided a light emitting unit emitting first light having a first wavelength and second light having a second wavelength, a photoreception unit outputting a first signal and a second signal depending on photoreception intensity of the first light and photoreception intensity of the second light transmitted through or reflected by biological tissue of a subject, a correlation coefficient acquisition unit acquiring a correlation coefficient between the first signal and the second signal, a transit time calculation unit calculating a transit time of blood in the biological tissue based on time-dependent change of the correlation coefficient, and an output unit outputting the concentration.

In such a structure, it is possible to measure the transit time of blood in the biological tissue of the subject using the principle of a pulse photometer without the need to administer an indicator to a blood flow. In addition, the transit time can be calculated using simple processing that acquires the correlation coefficient between the first signal and the second signal. Accordingly, biological information of the subject can be measured more easily using the principle of a pulse photometer.

The biological information measurement system according to the third aspect may further include a notifying unit making a notice when a value of the transit time falls outside a predetermined range.

In such a structure, the notice from the notifying unit helps to determine peripheral circulation incompetence. For example, when the value of the transit time falls below a predetermined range, the disease state of sepsis can be suspected.

DETAILED DESCRIPTION

Examples of embodiments will be described in detail below with reference to the attached drawings.

Figure 1:
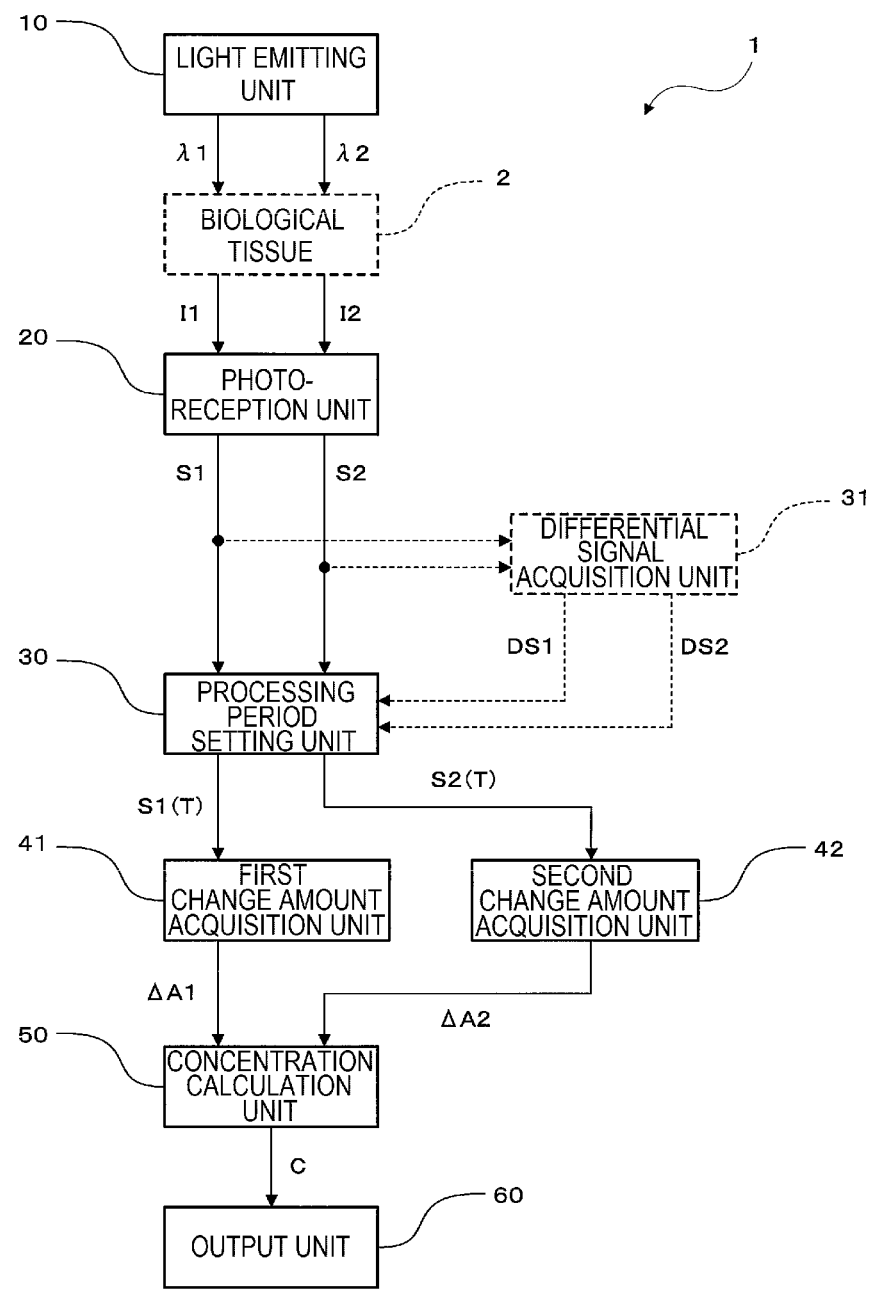
FIG. 1 is a block diagram illustrating a structure of a biological information measurement system according to a first embodiment.

FIG. 1 is a block diagram illustrating a functional structure of a biological information measurement system 1 (abbreviated below as the measurement system 1) according to a first embodiment.

The measurement system 1 includes a light emitting unit 10. The light emitting unit 10 is configured to emit first light having a first wavelength $\lambda 1$ and second light having a second wavelength $\lambda 2$. The first wavelength $\lambda 1$ is 880 nm or 940 nm, for example. The second wavelength $\lambda 2$ is 660 nm or 805 nm, for example. The first light is emitted from, for example, a semiconductor light emitting device. The second light is emitted from, for example, a semiconductor light emitting device. Examples of the semiconductor light emitting device are a light emitting diode (LED), laser diode, organic EL device, and the like.

The first wavelength $\lambda 1$ and second wavelength $\lambda 2$ are determined as appropriate depending on the type of light absorbing substance in blood for which the concentration is calculated. Examples of the light absorbing substance in blood are oxyhemoglobin, a dye (for example, indocyanine green) to be administered to a blood flow, and the like. Specifically, the wavelengths are determined so that the ratio of absorption coefficients of blood substantially differs depending on the concentration of the light absorber in blood.

The measurement system 1 includes a photoreception unit 20. The photoreception unit 20 is configured to output a first signal S1 depending on intensity I1 of the first light that has passed through or that is reflected by a biological tissue 2 of the subject. In addition, the photoreception unit 20 is configured to output a second signal S2 depending on intensity I2 of the second light that has passed through or that is reflected by the biological tissue 2 of the subject. The photoreception unit 20 is, for example, an optical sensor sensitive to the first wavelength $\lambda 1$ and the second wavelength $\lambda 2$. Examples of the optical sensor are a photodiode, phototransistor, photoresistor, and the like.

The measurement system 1 includes a processing period setting unit 30. The processing period setting unit 30 is configured to extract a signal cycle corresponding to the cardiac cycle of the subject for one of the first signal S1 and the second signal S2 and set the processing period in one of the first part in which the effect of arterial blood flowing to the biological tissue 2 is dominant and the second part in which the effect of venous blood flowing from the biological tissue 2 is dominant.

Figure 2A:
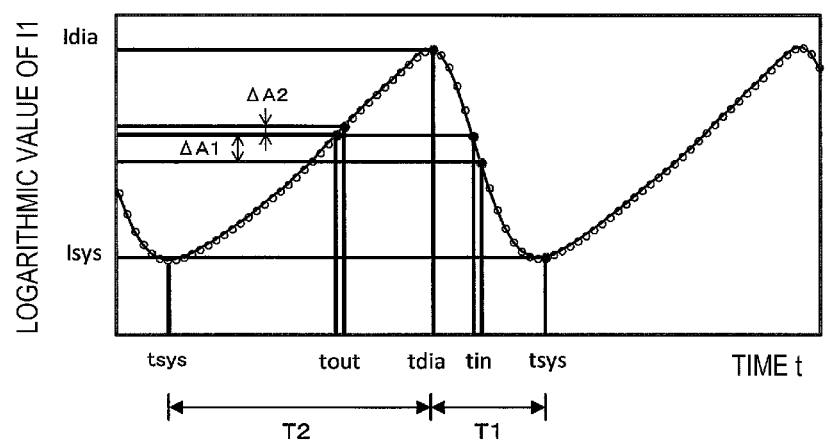
FIGS. 2A-B illustrate a process performed by the biological information measurement system in FIG. 1.

A case in which the above processing is performed for the first signal S1 will be described with reference to FIG. 2A. A waveform illustrated in FIG. 2A corresponds to time-dependent changes of the intensity of the first signal S1. As described above, the intensity of the first signal S1 corresponds to the intensity I1 of the first light in the photoreception unit 20. Accordingly, a horizontal axis in FIG. 2A represents time. A vertical axis represents a logarithmic value of the intensity I1 of the first light. The processing period setting unit 30 is configured to obtain the intensity of the first signal S1 at predetermined sampling periods. Each of a plurality of small circles indicated along the waveform represents the intensity of the first signal S1 obtained at each sampling point.

In FIG. 2A, a local maximal value of the logarithmic value is indicated as $I_{dia}$ and a local minimal value of the logarithmic value is indicated as $I_{sys}$. A time when the above logarithmic value becomes the local maximal value $I_{dia}$ is indicated as $t_{dia}$. A time when the above logarithmic value becomes the local minimal value $I_{sys}$ is indicated as $t_{sys}$. The processing period setting unit 30 is configured to treat the time period from the time $t_{dia}$ to the time $t_{dia}$ or the time period from the time $t_{sys}$ to the time $t_{sys}$ as the signal cycle corresponding to the cardiac cycle of the subject.

In the signal cycle, in a period T1 (an example of a first period) from the time $t_{dia}$ to the time $t_{sys}$ during which the intensity I1 of the first light reduces, the effect of arterial blood flowing to the biological tissue 2 is dominant. In addition, in a period T2 (an example of the second period) from the time $t_{sys}$ to the time $t_{dia}$ during which the intensity I1 of the first light increases, venous blood flowing from the biological tissue 2 is dominant. The processing period setting unit 30 is configured to set the processing period for acquiring the attenuation change amount, which will be described later, for one of the period T1 and the period T2. The processing period is determined to be shorter than the period T1 and the period T2 and is further determined to be at least one sampling period. In FIG. 2A, a processing period for the period T1 is shown as $t_{in}$. A processing period for the period T2 is shown as $t_{out}$.

Although not illustrated, the processing period setting unit 30 is configured to be able to perform the same processing for the second signal S2. The signal to be processed is determined as appropriate depending on the type of a light absorbing substance in blood for which the concentration is calculated.

The measurement system 1 includes a first change amount acquisition unit 41. The first change amount acquisition unit 41 is configured to obtain a first change amount ΔA1 corresponding to the attenuation change amount of the first light based on the first signal S1 (T) in the processing period set by the processing period setting unit 30.

When the processing period set by the processing period setting unit 30 is $t_{in}$ in the first period T1, the first change amount ΔA1 is obtained by the following expression.

$$\Delta A2 = \log[I2(t1)/I2(t2)]$$
$$= \log[I2(t1)] - \log[I2(t2)]$$

In this expression, t1 represents the starting point of the processing period $t_{in}$ and t2 represents the end point of the processing period $t_{in}$.

When the processing period set by the processing period setting unit 30 is $t_{out}$ in the second period T2, the first change amount ΔA1 is obtained by the following expression.

$$\Delta A2 = \log[I2(t4)/I2(t3)]$$
$$= \log[I2(t3)] - \log[I2(t3)]$$

In this expression, t3 represents the starting point of the processing period $t_{out}$ and t4 represents the end point of the processing period $t_{out}$.

The measurement system 1 includes a second change amount acquisition unit 42. The second change amount acquisition unit 42 is configured to obtain the second change amount ΔA2 corresponding to the attenuation change amount of the second light based on the second signal S2(T) in the processing period set by the processing period setting unit 30.

When the processing period set by the processing period setting unit 30 is $t_{in}$ in the first period T1, the second change amount ΔA2 is obtained by the following expression.

$$\Delta A1 = \log[I1(t1)/I1(t2)]$$
$$= \log[I1(t1)] - \log[I1(t2)]$$

In this expression, t1 represents the starting point of the processing period $t_{in}$ and t2 represents the end point of the processing period $t_{in}$.

When the processing period set by the processing period setting unit 30 is $t_{out}$ in the second period T2, the second change amount ΔA2 is obtained by the following expression.

$$\Delta A1 = \log[I1(t4)/I1(t3)]$$
$$= \log[I1(t4)] - \log[I1(t3)]$$

In this expression, t3 represents the starting point of the processing period $t_{out}$ and t4 represents the end point of the processing period $t_{out}$.

The measurement system 1 includes a concentration calculation unit 50. The concentration calculation unit 50 is configured to calculate a concentration C of a light absorbing substance in blood of the subject based on the first change amount ΔA1 obtained by the first change amount acquisition unit 41 and the second change amount ΔA2 obtained by the second change amount acquisition unit 42. Specifically, the concentration calculation unit 50 is configured to calculate a change amount ratio Φ, which is the ratio of the second change amount ΔA2 to the first change amount ΔA1. The concentration C of the light absorbing substance in blood is given by the following expression as a function of the change amount ratio Φ. The function f depends on the light absorbing substance in blood.

$$C = f(\Phi)$$

When the arterial blood oxygen saturation is calculated as the concentration of a light absorbing substance in blood, the ratio of oxyhemoglobin to the amount of hemoglobin capable of carrying oxygen is obtained. As this ratio increases, the ratio of deoxyhemoglobin reduces. That is, when the arterial blood oxygen saturation is calculated, the ratio of deoxyhemoglobin is treated as the concentration of a light absorbing substance in blood.

The measurement system 1 includes an output unit 60. The output unit 60 is configured to output the concentration C calculated by the concentration calculation unit 50. The output unit 60 may have various aspects. For example, the output unit 60 may be a display unit visually providing the concentration C. Alternatively, the output unit 60 may be configured to providing the concentration C as a voice output. Alternatively, the output unit 60 may be configured as a terminal capable of outputting a signal indicating the concentration C externally.

In the embodiment, the signal cycles corresponding to the cardiac cycles of the subject obtained based on the signal corresponding to the photoreception intensity in the photoreception unit 20 is divided into a portion in which the effect of arterial blood flowing to the biological tissue 2 is dominant and a portion in which the effect of venous blood flowing from the biological tissue 2 is dominant. The processing period is set for only one of both portions and the attenuation change amount of each light having each individual wavelength is obtained. The processing period is necessarily shorter than the diastole phase or the systole phase of the heart of the subject. That is, the concentration of a light absorbing substance in blood of the subject can be calculated at high speed while suppressing calculation loads. Accordingly, biological information can be measured easily using the principle of a pulse photometer.

As illustrated by dashed lines in FIG. 1, the measurement system 1 may include a differential signal acquisition unit 31. The differential signal acquisition unit 31 is configured to obtain a differential signal by differentiating one of the first signal S1 and the second signal S2 for which the processing period setting unit 30 sets the processing period. In FIG. 1, the differential signal of the first signal S1 is indicated as DS1 and the differential signal of the first signal S2 is indicated as DS2.

A case in which a differential signal DS1 is obtained from the first signal S1 will be described with reference to FIG. 2B. A waveform illustrated in FIG. 2B corresponds to the time-dependent change of the intensity of the differential signal DS1. As described above, the intensity of the differential signal DS1 corresponds to the differentiated value of the intensity I1 of the first light. Accordingly, a horizontal axis represents time in FIG. 2B. A vertical axis indicates the differentiated value of the logarithmic value of the intensity I1 of the first light.

Figure 2B:
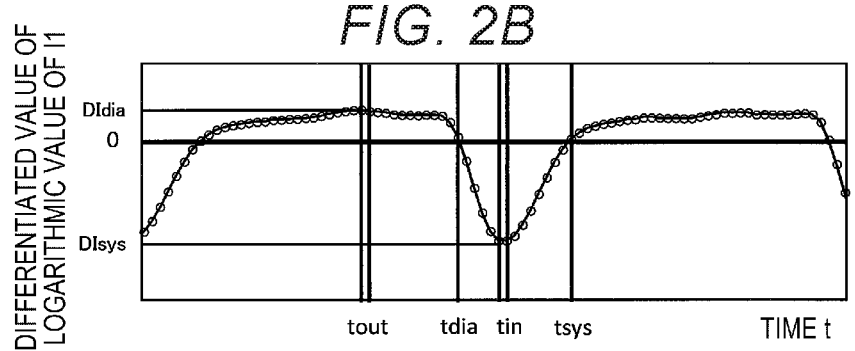

In FIG. 2B, a maximum value of the differentiated value is indicated as $DI_{dia}$ and a minimum value of the differentiated value is indicated as $DI_{sys}$. The differentiated value corresponds to the change in the amount (that is, the amount of blood flow) of blood through which the first light passes. Accordingly, the minimum value $DI_{sys}$ of the differentiated value indicates the point at which the ratio of the inflow amount of arterial blood to the outflow amount of venous blood becomes maximum. The maximum value $DI_{dia}$ of the differentiated value indicates the point at which the ratio of the outflow amount of venous blood to the inflow amount of arterial blood becomes maximum.

In this case, the processing period setting unit 30 is configured to set the processing period $t_{in}$ in the first period T1 of the cardiac cycle based on the minimum value of the differential signal DS1 corresponding to the minimum value $DI_{sys}$ of the differentiated value. For example, the processing period $t_{in}$ is determined to be shorter than the period T1 and to be at least one sampling period of the first signal S1 beginning with the time corresponding to the minimum value of the differential signal DS1.

In such a structure, only by performing simple processing that differentiates the first signal S1, the processing period $t_{in}$ can be set at the feature point at which the effect of arterial blood flowing to the biological tissue 2 is the most dominant. Accordingly, it is possible to improve the effect of the above structure that can easily measure biological information using the principle of the pulse photometer.

Alternatively, the processing period setting unit 30 is configured to set the processing period $t_{out}$ in the second period T2 of the cardiac cycle based on the maximum value of the differential signal DS1 corresponding to the maximum value $DI_{dia}$ of the differentiated value. For example, processing period $t_{out}$ is determined to be shorter than the period T2 and to be at least one sampling period of the first signal S1 beginning with the time corresponding to the maximum value of the differential signal DS1.

In such a structure, only by performing simple processing that differentiates the first signal S1, the processing period $t_{out}$ can be set at the feature point at which the effect of venous blood flowing from the biological tissue 2 is the most dominant. Accordingly, it is possible to improve the effect of the above structure that can easily measure biological information using the principle of the pulse photometer.

Although not illustrated, the differential signal acquisition unit 31 is configured to be able to perform the same processing for the second signal S2. The signal to be processed is determined as appropriate depending on the type of a light absorbing substance in blood for which the concentration is calculated.

In the measurement system 1, the functions of the processing period setting unit 30, the differential signal acquisition unit 31, the first change amount acquisition unit 41, the second change amount acquisition unit 42, and the concentration calculation unit 50 are provided by software executed by a combination of a processor and a memory interconnected communicably. Examples of the processor include a central processing unit (CPU) and a microprocessor unit (MPU). Examples of the memory include a random access memory (RAM) and read-only memory (ROM). However, at least one of the functions of the processing period setting unit 30, the differential signal acquisition unit 31, the first change amount acquisition unit 41, the second change amount acquisition unit 42, and the concentration calculation unit 50 may be provided by hardware such as circuit devices or a combination of hardware and software.

Figure 3:
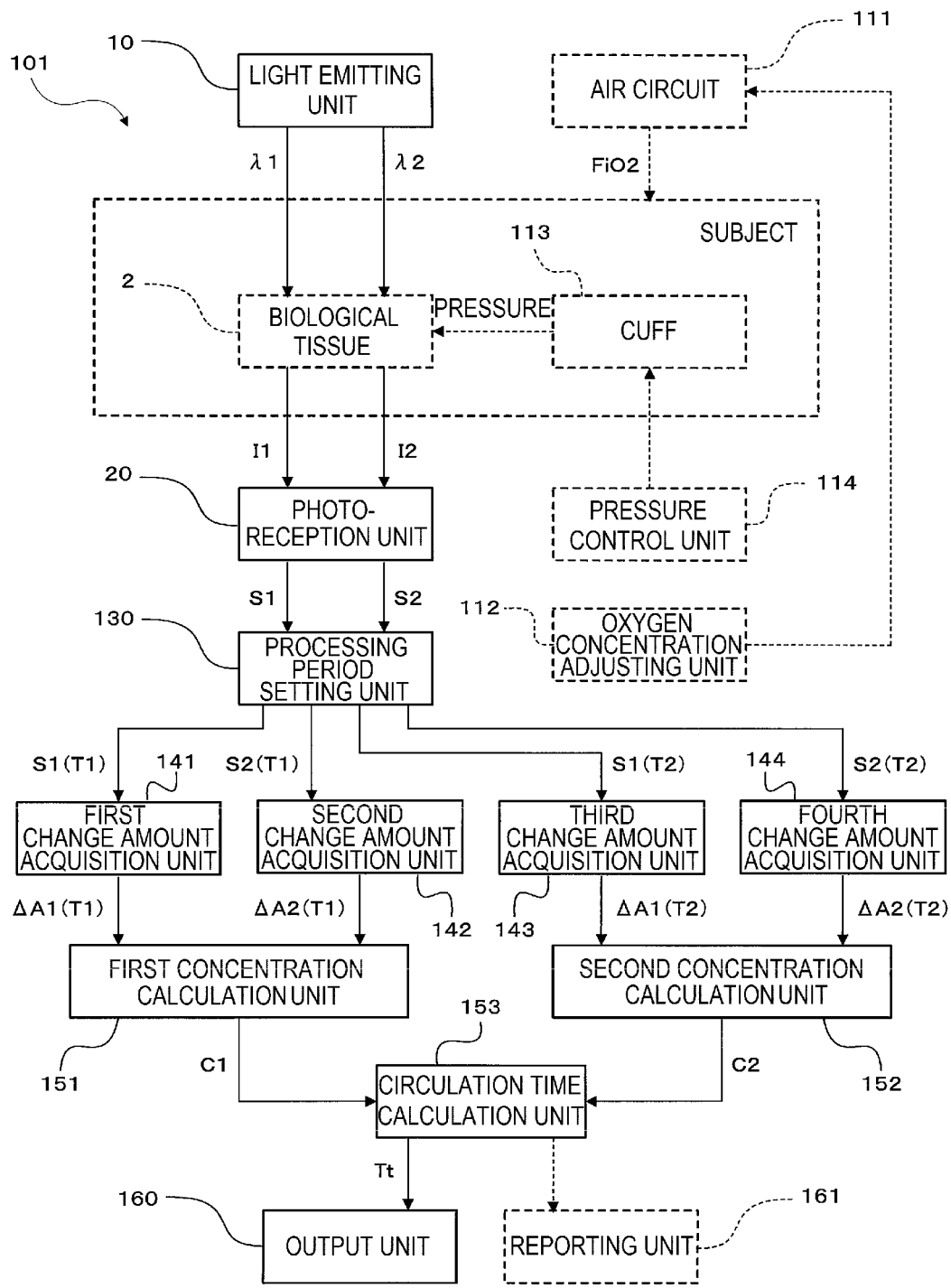
FIG. 3 is a block diagram illustrating a structure of a biological information measurement system according to a second embodiment.

FIG. 3 is a block diagram illustrating the functional structure of a biological information measurement system 101 (abbreviated hereinafter as the measurement system 101) according to a second embodiment. Components having the same structures or functions as in the measurement system 1 according to the first embodiment are given the same reference numerals and duplicate descriptions are omitted.

Figure 4A:
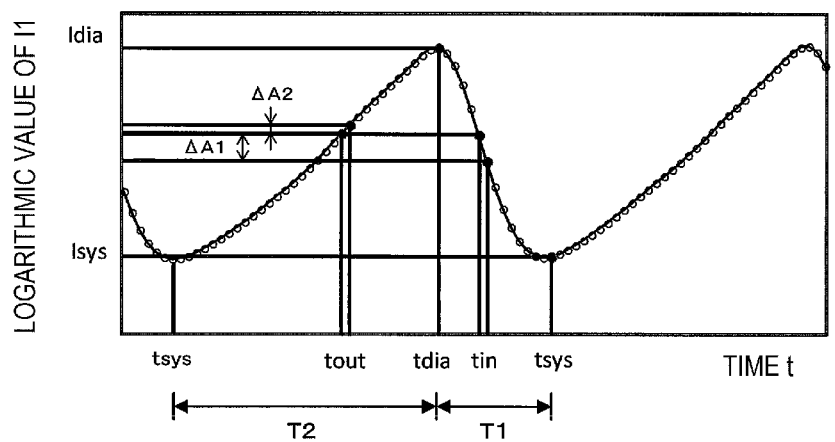
FIGS. 4A-B illustrate a process performed by the biological information measurement system in FIG. 3.

The measurement system 101 includes a processing period setting unit 130. The processing period setting unit 130 is configured to extract the signal cycle corresponding to the cardiac cycle of the subject for each of the first signal S1 and the second signal S2. The case in which the above processing is performed for the first signal S1 will be described with reference to FIG. 4A. Since FIG. 4A is identical to FIG. 2A, duplicate descriptions are omitted. The processing period setting unit 130 is configured to be able to perform the same processing for the second signal S2.

The processing period setting unit 130 is configured to assume the time period from the time $t_{dia}$ to the time $t_{dia}$ or the time period from the time $t_{sys}$ to the time $t_{sys}$ as the signal cycle corresponding to the cardiac cycle of the subject. The processing period setting unit 130 is configured to set the first processing period $t_{in}$ in the first period T1 in which arterial blood flowing to the biological tissue 2 is dominant and set the second processing period $t_{out}$ in the second period T2 in which venous blood flowing from the biological tissue 2 is dominant. The processing period is determined to be shorter than the period T1 and the period T2 and to be at least one sampling period.

In the setting of the first processing period and the second processing period, it is possible to apply the structure and function of the differential signal acquisition unit 31 described with reference to the measurement system 1 according to the first embodiment.

The measurement system 101 includes a first change amount acquisition unit 141. The first change amount acquisition unit 141 is configured to obtain the first change amount $\Delta A1$ corresponding to the attenuation change amount of the first light in the first processing period $t_{in}$ set by the processing period setting unit 130 based on the first signal S1 (T1) in the first processing period $t_{in}$. The first change amount $\Delta A1$ is obtained by the following expression.

$$\Delta A1 = \log[I1(t1)/I1(t2)]$$
$$= \log[I1(t1)] - \log[I1(t2)]$$

In this expression, t1 represents the starting point of the first processing period $t_{in}$ and t2 represents the end point of the first processing period $t_{in}$.

The measurement system 101 includes a second change amount acquisition unit 142. The second change amount acquisition unit 142 is configured to obtain the second change amount $\Delta A2$ corresponding to the attenuation change amount of the second light in the first processing period $t_{in}$ set by the processing period setting unit 130 based on the second signal S2 (T1) in the first processing period $t_{in}$. The second change amount $\Delta A2$ is obtained by the following expression.

$$\Delta A2 = \log[I2(t1)/I2(t2)]$$
$$= \log[I2(t1)] - \log[I2(t2)]$$

In this expression, t1 represents the starting point of the processing period $t_{in}$ and t2 represents the end point of the first processing period $t_{in}$.

The measurement system 101 includes a third change amount acquisition unit 143. The third change amount acquisition unit 143 is configured to obtain a third change amount $\Delta A3$ corresponding to the attenuation change amount of the first light in the second processing period $t_{out}$ set by the processing period setting unit 130 based on the first signal S1 (T2) in the second processing period $t_{out}$. The third change amount $\Delta A3$ is obtained by the following expression.

$$\Delta A3 = \log[I1(t4)/I1(t3)]$$
$$= \log[I1(t4)] - \log[I1(t3)]$$

In this expression, t3 represents the starting point of the second processing period $t_{out}$ and t4 represents the end point of the second processing period $t_{out}$.

The measurement system 101 includes a fourth change amount acquisition unit 144. The fourth change amount acquisition unit 144 is configured to obtain a fourth change amount $\Delta A4$ corresponding to the attenuation change amount of the second light in the second processing period $t_{out}$ set by the processing period setting unit 130 based on the second signal S2 (T2) in the second processing period $t_{out}$. The fourth change amount $\Delta A4$ is obtained by the following expression.

$$\Delta A4 = \log[I2(t4)/I2(t3)]$$
$$= \log[I2(t3)] - \log[I2(t3)]$$

In this expression, t3 represents the starting point of the processing period $t_{out}$ and t4 represents the end point of the processing period $t_{out}$.

The measurement system 101 includes a first concentration calculation unit 151. The first concentration calculation unit 151 is configured to obtain the first concentration C1 corresponding to the concentration of a light absorbing substance in blood of the subject in the first the first processing period $t_{in}$ based on the first change amount $\Delta A1$ obtained by the first change amount acquisition unit 141 and the second change amount $\Delta A2$ obtained by the second change amount acquisition unit 142. Specifically, the first concentration calculation unit 151 is configured to calculate a first change amount ratio $\Phi_{in}$, which is the ratio of the second change amount $\Delta A2$ to the first change amount $\Delta A1$. The first concentration C1 is given by the following expression as a function of the first change amount ratio $\Phi_{in}$. The function f1 depends on the light absorbing substance in blood.

$$C1 = f1(\Phi_{in})$$

The measurement system 101 includes a second concentration calculation unit 152. The second concentration calculation unit 152 is configured to calculate a second concentration C2 corresponding to the concentration of a light absorbing substance in blood of the subject in the second processing period $t_{out}$ based on the third change amount $\Delta A3$ obtained by the third change amount acquisition unit 143 and the fourth change amount $\Delta A4$ obtained by the fourth change amount acquisition unit 144. Specifically, the second concentration calculation unit 152 is configured to calculate a second change amount ratio $\Phi_{out}$, which is the ratio of the fourth change amount $\Delta A4$ to the third change amount $\Delta A3$. The second concentration C2 is given by the following expression as a function of the second change amount ratio $\Phi_{out}$. The function f2 depends on the light absorbing substance in blood.

$$C2 = f2(\Phi_{out})$$

The measurement system 101 includes a transit time calculation unit 153. The transit time calculation unit 153 is configured to calculate a transit time Tt of blood in the biological tissue 2 based on the first concentration C1 calculated by the first concentration calculation unit 151 and the second concentration C2 calculated by the second concentration calculation unit 152.

Figure 4B:
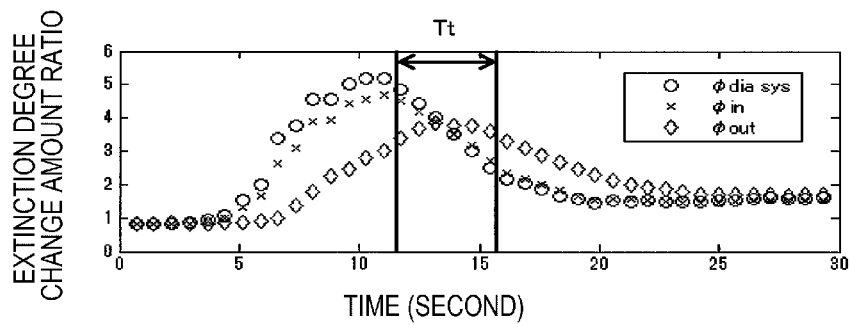

FIG. 4B illustrates the operation of the transit time calculation unit 153. FIG. 4B illustrates the time-dependent change of the first change amount ratio $\Phi_{in}$ corresponding to the first concentration C1 and the second change amount ratio $\Phi_{out}$ corresponding to the second concentration C2. Circles FIG. 4B indicate the time-dependent change of the attenuation change amount obtained by a conventional pulse photometer as a comparison example. In the conventional pulse photometer, between the time (that is, $t_{dia}$) when the photoreception intensity in the photoreception unit becomes the maximum and the time (that is, $t_{sys}$) when the photoreception intensity becomes the minimum, the attenuation is obtained for each of light having each wavelength and the attenuation ratio is calculated. Here, 940 nm is selected as the first wavelength λ1 and 805 nm is selected as the second wavelength λ2. The first change amount ratio $\Phi_{in}$ and the second change amount ratio $\Phi_{out}$ are calculated by the following expressions.

$$\Phi_{in} = \Delta A2/\Delta A1$$

$$\Phi_{out} = \Delta A4/\Delta A3$$

The time-dependent change of the first change amount ratio $\Phi_{in}$ in which the effect of arterial blood flowing to the biological tissue 2 is dominant is similar, in principle, to the time-dependent change of the change amount ratio calculated by a conventional pulse photometer. However, the time-dependent change of the second change amount ratio $\Phi_{out}$ in which the effect of venous blood flowing from the biological tissue 2 is dominant is significantly different from the time-dependent change of the first change amount ratio $\Phi_{in}$. Specifically, the second change amount ratio $\Phi_{out}$ increases monotonically and reduces monotonically behind the first change amount ratio $\Phi_{in}$. This time delay corresponds to the transit time of blood Tt in the biological tissue 2 to be calculated.

The measurement system 101 includes an output unit 160. The output unit 160 is configured to output at least one of the first concentration C1 calculated by the first concentration calculation unit 151, the second concentration C2 calculated by the second concentration calculation unit 152, and the transit time Tt calculated by the transit time calculation unit 153. The output unit 160 may have various aspects. For example, the output unit 160 may be a display unit visually providing at least one of the first concentration C1, the second concentration C2, and the transit time Tt. Alternatively, the output unit 160 may be configured to provide at least one of the first concentration C1, second concentration C2, and the transit time Tt as a voice output. Alternatively, the output unit 160 may be configured as a terminal capable of outputting a signal indicating at least one of the first concentration C1, second concentration C2, and the transit time Tt.

Conventionally, an indicator dilution method has been used to measure the transit time. A dye is often used as an indicator. The dye is administered upstream of a blood flow to be transferred to the biological tissue to draw the dye densitogram indicating the time-dependent change of the concentration of the dye in blood for each of the blood vessel through which the blood flows to the biological tissue and the blood vessel through which the blood flows from the biological tissue.

Figure 5A:
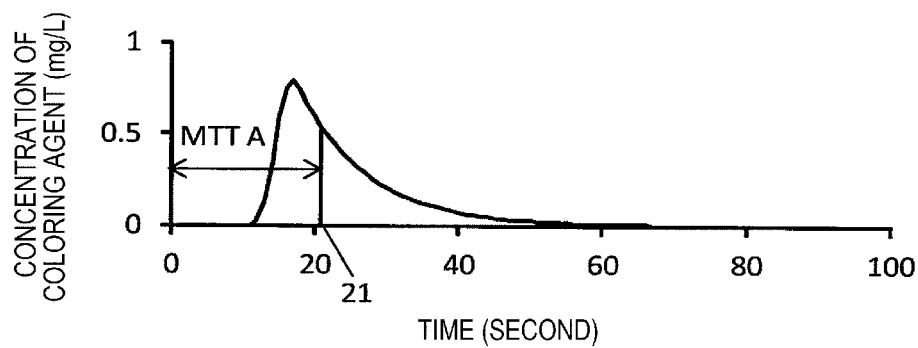
FIGS. 5A-C illustrate a process performed by the biological information measurement system in FIG. 3.

When the concentration of the dye is measured at a measurement point A from which arterial blood flows to the biological tissue, a dye densitogram as illustrated in FIG. 5A is acquired. The dye is administered at time 0. The administered dye is transferred to the biological tissue while being diffused by a blood flow. The dye densitogram obtained at the measurement point A has a curve that increases monotonically, reduces monotonically, and has a single peak. The time period from the time when the dye is administered and the time when the area under the curve (AUC) is halved is referred to as a mean transit time (MTT). In FIG. 5A, the mean transit time at the measurement point A is indicated as MTTA.

Figure 5B:
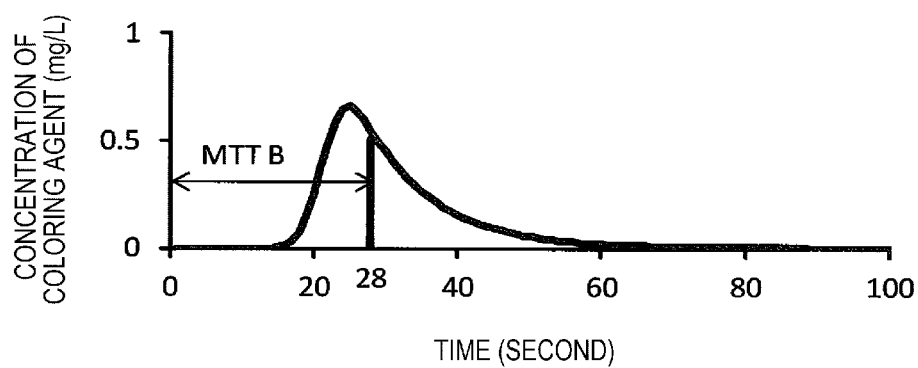

The dye having been transmitted the biological tissue appears at a measurement point B at which venous blood flows. When the concentration of the dye is measured at the measurement point B, a dye densitogram as illustrated in FIG. 5B is obtained. The dye is administered at time 0. The concentration increases monotonically behind the measurement point A and the peak of the curve is reduced by the amount of diffusion. In FIG. 5B, the mean transit time at the measurement point B is indicated as MTTB.

Since the dye does not disappear after being transmitted through the biological tissue, the area under the curve at the measurement point A is the same as the area under the curve at the measurement point B. The time difference (MTT A to B) between MTTA and MTTB in FIG. 5C corresponds to the time for the dye to be transmitted through the biological tissue, that is, the transit time of blood in the biological tissue.

If a catheter is inserted into the measurement point A and the measurement point B and the concentration of the dye is measured while drawing blood continuously (a cuvette method), the transit time of blood equivalent to the time difference between MTTA and MTTB is obtained. However, invasion with a catheter gives excessive loads to the subject.

The pulse dye dilution method has been known as a non-invasive method. In this method, the concentration of a dye in arterial blood is measured continuously using the principle of a pulse photometer. However, this method can obtain only the concentration of the dye in arterial blood. Accordingly, MTTA can be obtained, but the time difference between MTTA and MTTB cannot be obtained. The curve illustrated as a comparison example in FIG. 4B corresponds to the dye densitogram obtained by the pulse dye dilution method.

In the embodiment, the signal cycle corresponding to the cardiac cycle of the subject obtained based on the signal corresponding to the photoreception intensity in the photoreception unit 20 is divided into a portion in which the effect of arterial blood flowing to the biological tissue 2 is dominant and a portion in which the effect of venous blood flowing from the biological tissue 2 is dominant. An attenuation change amount of each light having each wavelength is obtained for both portions, so that two types of concentrations of light absorbing substance in blood having different time-dependent change characteristics are obtained as in the dye densitograms illustrated in FIGS. 5A and 5B. This enables the calculation of the transit time Tt of blood in the biological tissue 2 while using the principle of a pulse photometer without invasion.

The first processing period and the second processing period are necessarily shorter than the diastole phase or the systole phase of the heart of the subject. That is, the concentration of a light absorbing substance in blood and the transit time of blood of the subject can be calculated at high speed while suppressing calculation loads. Accordingly, biological information can be measured easily using the principle of a pulse photometer.

Some examples can be considered as methods for obtaining the transit time Tt based on the first change amount ratio $\Phi_{in}$ corresponding to the first concentration C1 and the second change amount ratio $\Phi_{out}$ corresponding to the second concentration C2 illustrated in FIG. 4B.

Figure 5C:
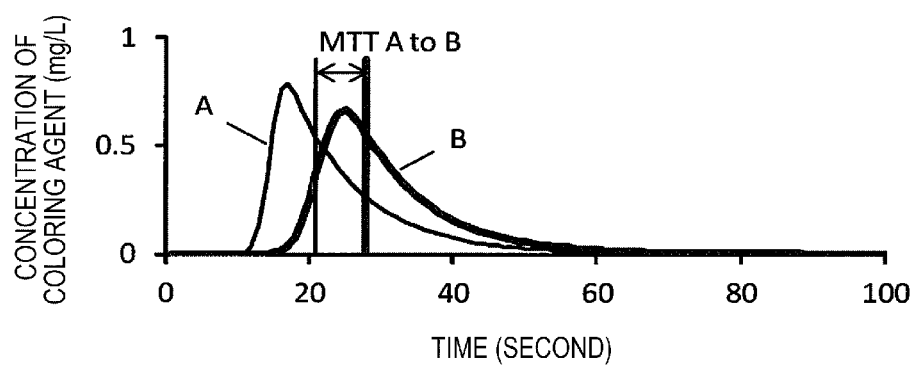

In the example illustrated in FIG. 4B, the transit time Tt is calculated based on the difference in the mean transit time obtained from the time-dependent change of the change amount ratios as in the example illustrated in FIG. 5C. Specifically, the time period until the area under the curve (AUC) is halved is obtained as the second mean transit time from the time-dependent change of the first change amount ratio $\Phi_{in}$. Similarly, the time period until the area under the curve (AUC) is halved is obtained as the second mean transit time from the time-dependent change of the second change amount ratio $\Phi_{out}$. The transit time Tt is calculated as the difference between the first mean transit time and the second mean transit time.

Alternatively, the transit time Tt may calculated based on the time difference between the time when the first change amount ratio $\Phi_{in}$ becomes the maximum value and the time when the second change amount ratio $\Phi_{out}$ becomes the maximum value.

Alternatively, the transit time Tt may calculated based on the time difference between a time when the first change amount ratio $\Phi_{in}$ exceeds a predetermined threshold and a time when the second change amount ratio $\Phi_{out}$ exceeds the predetermined threshold. In this case, the threshold needs to be set to a value lower than the maximum value of the second change amount ratio $\Phi_{out}$, which is lower than the maximum value of the first change amount ratio $\Phi_{in}$.

Alternatively, the transit time Tt may be calculated based on a cross correlation function between the first change amount ratio $\Phi_{in}$ and the second change amount ratio $\Phi_{out}$. Since the time-dependent change characteristics of the first change amount ratio $\Phi_{in}$ are similar to the time-dependent change characteristics of the second change amount ratio $\Phi_{out}$, a time period from a reference time related to the first change amount ratio $\Phi_{in}$ to the time when the maximum value of the cross correlation function is obtained can be assumed to be the delay in the time-dependent change of the second change amount ratio $\Phi_{out}$ from the time-dependent change of the first change amount ratio $\Phi_{in}$. This delay is calculated as the transit time Tt.

The transit time Tt can be also calculated based on the time-dependent change of the arterial blood oxygen saturation. Such examples will be described below.

As illustrated by dashed lines in FIG. 3, the measurement system 101 may include an air circuit 111 and an oxygen concentration adjusting unit 112. In this case, the air circuit 111 is configured to be able to supply air to be inhaled by the subject. The oxygen concentration adjusting unit 112 is configured to adjust an oxygen concentration FiO2 included in air to be supplied via the air circuit 111.

Figure 6A:
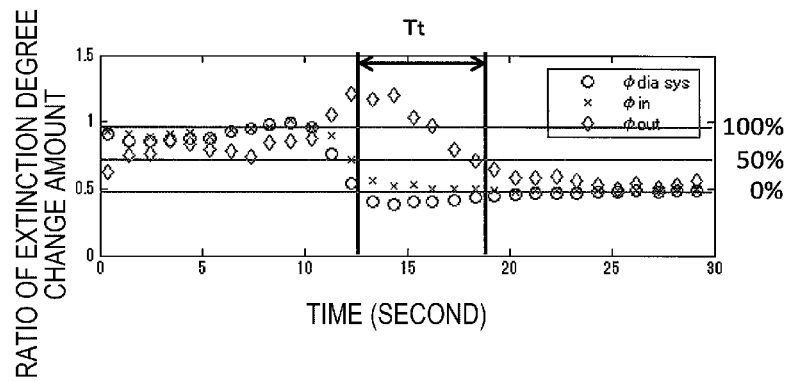
FIGS. 6A-B illustrate a process performed by the biological information measurement system in FIG. 3.

The oxygen concentration adjusting unit 112 reduces the oxygen concentration FiO2 in air to be inhaled by the subject, for a predetermined period. After that, the oxygen concentration adjusting unit 112 returns the oxygen concentration FiO2 to the normal value. FIG. 6A illustrates the time-dependent change of the first change amount ratio corresponding to the first concentration C1 calculated by the first concentration calculation unit 151 and the second change amount ratio $\Phi_{out}$ corresponding to the second concentration C2 calculated by second concentration C2. Here, 940 nm is selected as the first wavelength $\lambda 1$ and 660 nm is selected as the second wavelength $\lambda 2$. The first change amount ratio $\Phi_{in}$ and the second change amount ratio $\Phi_{out}$ are calculated by the following expression.

$$\Phi_{in} = \Delta A2/\Delta A1$$

$$\Phi_{out} = \Delta A4/\Delta A3$$

The first change amount ratio $\Phi_{in}$ and the second change amount ratio $\Phi_{out}$ have a negative correlation with respect to the arterial blood oxygen saturation. Accordingly, reduction in the first change amount ratio $\Phi_{in}$ and the second change amount ratio $\Phi_{out}$ indicates an increase in the arterial blood oxygen saturation. Accordingly, these change amount ratios increase as the oxygen concentration FiO2 reduces and these change amount ratios reduce as the concentration of oxygen FiO2 increases. As in the example described above, the time-dependent change of the first change amount ratio in which the effect of arterial blood flowing to the biological tissue 2 is dominant is similar to the time-dependent change of the change amount ratio calculated by a conventional pulse photometer. However, the time-dependent change of the second change amount ratio $\Phi_{out}$ in which the effect of venous blood flowing from the biological tissue 2 is dominant is significantly different from the time-dependent change of the first change amount ratio $\Phi_{in}$. Specifically, the second change amount ratio $\Phi_{out}$ increases monotonically and reduces monotonically behind the first change amount ratio $\Phi_{in}$.

In this example, if the value when the first change amount ratio $\Phi_{in}$ starts reducing is 100% and the value when the first change amount ratio $\Phi_{in}$ ends reducing is 0%, the time difference between the time when the first change amount ratio $\Phi_{in}$ reduces to the value corresponding to 50% and the time when the second change amount ratio $\Phi_{out}$ reduces to the value corresponding to 50% is calculated as the transit time Tt.

Reduction in the oxygen concentration FiO2 by the oxygen concentration adjusting unit 112 can be considered as pseudo reproduction of the state in which the subject holds the breath. Accordingly, if the subject awakes, the above change of the arterial blood oxygen saturation can also be caused by having the subject to hold the breath. In addition, the above change of the arterial blood oxygen saturation can also be caused by having the subject to raise the hand in the state in which the light emitting unit 10 and the photoreception unit 20 are attached to the tissue of the fingertip of the subject.

In such a structure, it is possible to measure the transit time Tt of blood in the biological tissue 2 of the subject using the principle of a pulse photometer without the need to administer an indicator to a blood flow. Accordingly, biological information of the subject can be measured more easily using the principle of a pulse photometer. In addition, it is possible to obtain the change history of the transit time Tt by adjusting the concentration of oxygen using the oxygen concentration adjusting unit 112 at regular time intervals and calculating the transit time Tt. This notifies the trend of the deterioration and improvement in peripheral circulation of the subject.

As illustrated by dashed lines in FIG. 3, the measurement system 101 may include a cuff 113 and a pressure control unit 114. In this case, the cuff 113 can be attached to the subject so as to press a blood flow upstream side of the biological tissue 2 of the subject. For example, when the light emitting unit 10 and the photoreception unit 20 are attached to a tip of a finger, the cuff 113 is attached to a blood flow upstream side of the finger (for example, the part between the second joint and the third joint) and the pressure control unit 114 is configured to be able to control the pressure of the cuff 113.

The pressure control unit 114 raises the pressure of the cuff 113 by blowing air to the cuff 113. When the pressure of the cuff 113 reaches a predetermined value, the pressure control unit 114 keeps this state for a predetermined time.

Figure 6B:
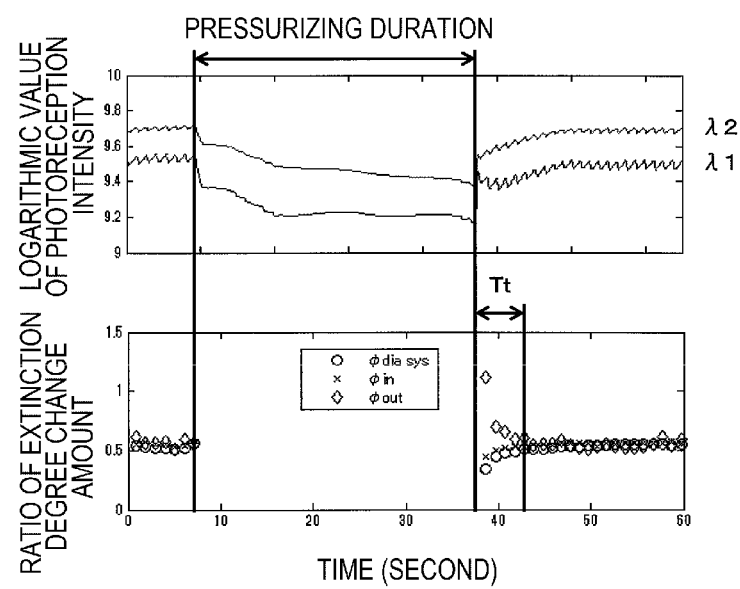

This presses the part to which the cuff 113 has been attached. After an elapse of the predetermined time, the pressure control unit 114 releases the pressure of the cuff 113. FIG. 6B illustrates the time-dependent change of the first change amount ratio $\Phi_{in}$ corresponding to the first concentration C1 calculated by the first concentration calculation unit 151 and the second change amount ratio $\Phi_{out}$ corresponding to the second concentration C2 calculated by the second concentration calculation unit 152, in this case. For the same components as in FIG. 6A, duplicate descriptions are omitted.

Since the blood flow stops during pressing, the first signal S1 and the second signal S2 having the signal cycle corresponding to the cardiac cycle are not obtained. Accordingly, the first change amount ratio $\Phi_{in}$ and the second change amount ratio $\Phi_{out}$ are not also obtained. When the pressure of the cuff 113 is released, the first change amount ratio $\Phi_{in}$ is greatly separated from the second change amount ratio $\Phi_{out}$ in the signal cycle corresponding to the first heartbeat. This separation is caused by the difference in the oxygen saturation between arterial blood and venous blood. Immediately after release from the pressing, the oxygen saturation of the biological tissue 2 including venous blood is low. Venous blood having high oxygen saturation flows in the biological tissue 2. As blood having small oxygen saturation flows out, the difference between the first change amount ratio $\Phi_{in}$ and the second change amount ratio $\Phi_{out}$ reduces. The time period from the release from pressing to a steady state in which the difference between both ratios is substantially zero is calculated as the transit time Tt. The time when the steady state is reached may be, for example, the time when the difference between the first change amount ratio $\Phi_{in}$ and the second change amount ratio $\Phi_{out}$ is equal to or less than a predetermined threshold.

Also in such a structure, it is possible to measure the transit time Tt of blood in the biological tissue 2 of the subject using the principle of a pulse photometer without the need to administer an indicator to a blood flow. Accordingly, biological information of the subject can be measured more easily using the principle of a pulse photometer. In addition, it is possible to obtain the change history of the transit time Tt by adjusting the pressure of the cuff 113 using the pressure control unit 114 at regular time intervals and calculating the transit time Tt. This notifies the trend of the deterioration and improvement in peripheral circulation of the subject.

As illustrated by dashed lines in FIG. 3, the measurement system 101 may include a notifying unit 161. The notifying unit 161 is configured to notify when the value of the transit time Tt calculated by the transit time calculation unit 153 is outside a predetermined range. The notifying unit 161 may have various aspects. For example, the notifying unit 161 visually notifies the fact that the value of the transit time Tt calculated by the transit time calculation unit 153 is outside the predetermined range. Alternatively, the notifying unit 161 provides the fact as a voice output. Alternatively, the notifying unit 161 outputs a signal indicating the fact externally.

In such a structure, notification from the notifying unit 161 assists diagnosis of peripheral circulation incompetence. For example, when the value of the transit time Tt falls below a predetermined range, the disease state of sepsis may be suspected.

In the disease state of sepsis, the expansion of arteries and arteriols, reduction of peripheral artery resistance, and increase in the amount of cardiac output first arise. This stage is referred to as a warm shock. Since the blood flows from artery to vein bypassing blood capillary in this state, oxygen in the peripheral tissue becomes insufficient. Such a blood flow bypassing blood capillary is referred to as a shunt blood flow. When this disease state progresses, the amount of cardiac output reduces, the blood pressure reduces, and shock disease occurs. In this stage, metabolic disorder occurs in the peripheral tissue. Accordingly, it is important to find the disease state in the stage of the warm shock and start treatment in an early stage. Since the blood flow does not pass through the peripheral tissue when a shunt blood flow is present, the difference in the oxygen saturation between artery and vein is small. Accordingly, the transit time of blood in the peripheral tissue becomes short. In the above structure, the early detection of the disease state of sepsis can be helped using simple measurement that uses the principle of a pulse photometer.

In the measurement system 101, the functions of the processing period setting unit 130, the first change amount acquisition unit 141, the second change amount acquisition unit 142, the third change amount acquisition unit 143, the fourth change amount acquisition unit 144, the first concentration calculation unit 151, the second concentration calculation unit 152, and the transit time calculation unit 153 are provided by software executed by a combination of a processor and a memory interconnected communicably. Examples of the processor are a CPU and MPU. Examples of the memory are a RAM and ROM. However, at least one of the functions of the processing period setting unit 130, the first change amount acquisition unit 141, the second change amount acquisition unit 142, the third change amount acquisition unit 143, the fourth change amount acquisition unit 144, the first concentration calculation unit 151, the second concentration calculation unit 152, and the transit time calculation unit 153 may be provided by hardware such as circuit devices or a combination of hardware and software.

Figure 7:
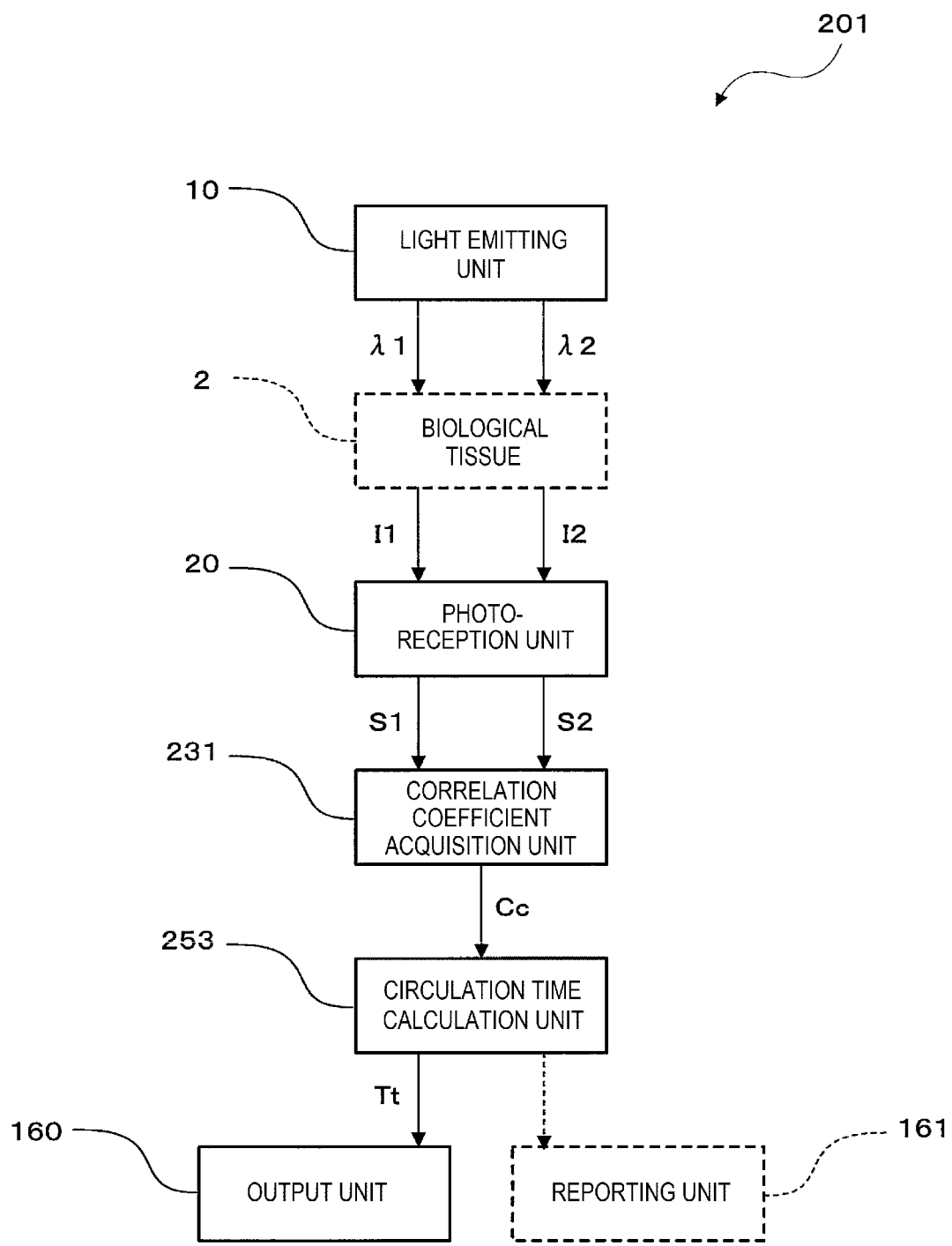
FIG. 7 is a block diagram illustrating a structure of a biological information measurement system according to a third embodiment.

FIG. 7 is a block diagram illustrating the functional structure of a biological information measurement system 201 (abbreviated below as the measurement system 201) according to a third embodiment. Components having the same structures or functions as in the measurement system 1 according to the first embodiment and the measurement system 101 according to the second embodiment are given the same reference numerals and duplicate descriptions are omitted.

The measurement system 201 includes a correlation coefficient acquisition unit 231. The correlation coefficient acquisition unit 231 is configured to obtain a correlation coefficient Cc between the first signal S1 and the second signal S2 output from the photoreception unit 20.

The measurement system 201 includes a transit time calculation unit 253. The transit time calculation unit 253 is configured to calculate the transit time Tt of blood in the biological tissue 2 based on the correlation coefficient Cc obtained by the correlation coefficient acquisition unit 231.

The measurement system 101 according to the second embodiment calculates the transit time Tt using the difference in the concentration of a light absorbing substance in blood between the blood flowing to the biological tissue 2 and the blood flowing from the biological tissue 2. The present embodiment focuses on the difference between the waveform of the first signal S1 in the signal cycle corresponding to the cardiac cycle of the subject and the waveform of the second signal S2 in the signal cycle and calculates the transit time Tt based on the difference.

Figure 8A:
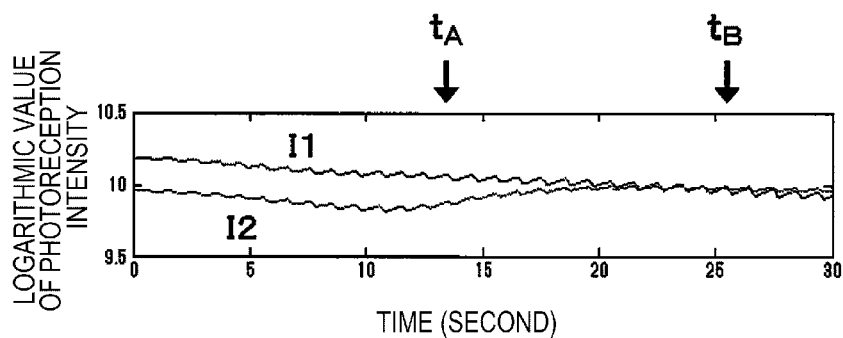
FIGS. 8A-G illustrate a process performed by the biological information measurement system in FIG. 7.

FIG. 8A illustrates the time-dependent change of the logarithmic value of the intensity I1 of the first light and the logarithmic value of the intensity I2 of the second light when the subject is caused to stop the breath and then caused to resume the breath after a predetermined time. In this case, 940 nm is selected as the first wavelength λ1 and 660 nm is selected as the second wavelength λ2. Substantially in the middle in the horizontal direction of FIG. 8A, it can be seen that the direct current component of the intensity I2 increases. The increase is caused since the blood in which the oxygen saturation has been raised by resumption of the breath reaches the biological tissue 2.

Figure 8B:
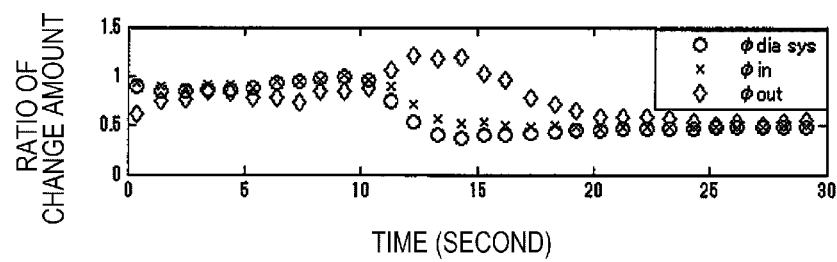

FIG. 8B illustrates the time-dependent change of the first change amount ratio and the second change amount ratio $\Phi_{out}$ measured by the measurement system 201 according to the second embodiment in this case.

Figure 8C:
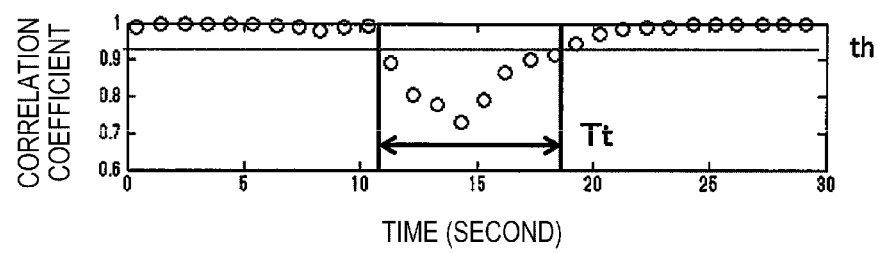

FIG. 8C illustrates the time-dependent change of the correlation coefficient between the time-dependent change waveform for the intensity I1 and the time-dependent change waveform for the intensity I2 illustrated in FIG. 8A. As the comparison in FIG. 8B illustrates, the correlation coefficient Cc drops in the period in which the first change amount ratio $\Phi_{in}$ differs from the second change amount ratio $\Phi_{out}$. That is, when there is a difference in the oxygen saturation between the blood flowing to the biological tissue 2 and the blood flowing from the biological tissue 2, the time-dependent change waveform for the intensity I1 is not similar to the time-dependent change waveform for the intensity I2.

Figure 8D:
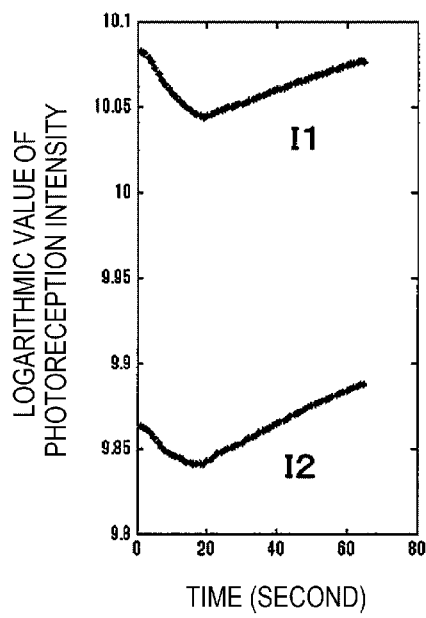
Figure 8E:
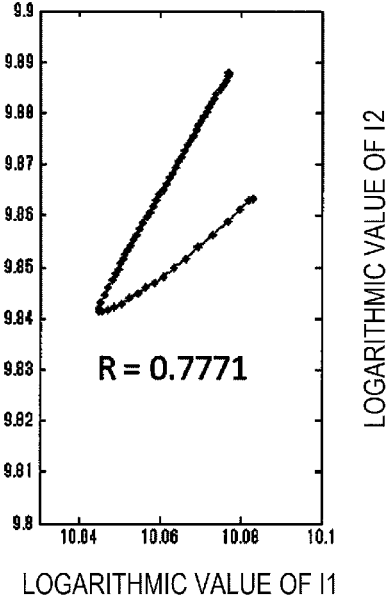

FIG. 8D is an enlarged view of a portion (one signal cycle) indicated by symbol $t_A$ in FIG. 8A. This portion corresponds to the signal cycle in which the correlation coefficient Cc is low. FIG. 8E illustrates a Lissajous waveform indicating the time-dependent change of the logarithmic value of the intensity I1 and the logarithmic value of the intensity I2 when the logarithmic value of the intensity I1 is plotted on the horizontal axis and the logarithmic value of the intensity I2 is plotted on the vertical axis.

Figure 8F:
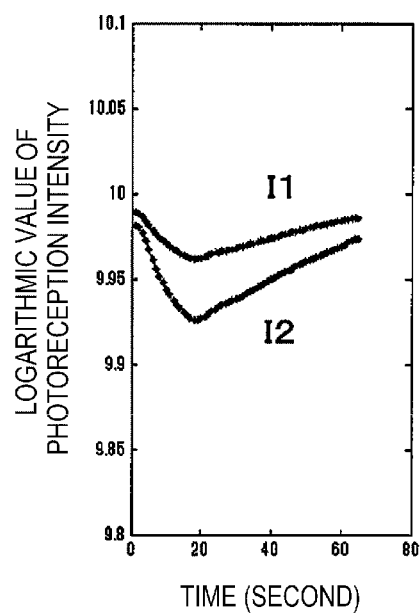
Figure 8G:
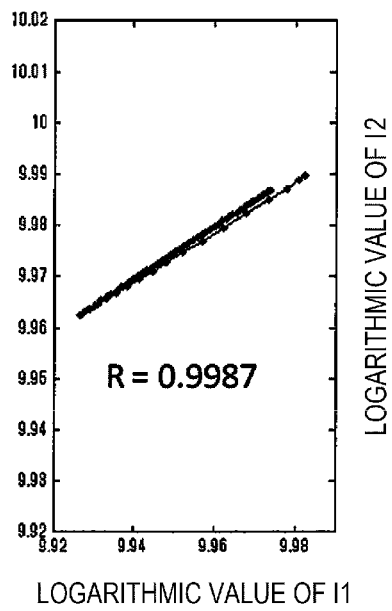

FIG. 8F is an enlarged view of a portion (one signal cycle) indicated by symbol $t_B$ in FIG. 8A. This portion corresponds to the signal cycle in which the correlation coefficient Cc is high. FIG. 8G illustrates a Lissajous waveform corresponding to FIG. 8E.

As illustrated in FIG. 8E, when the correlation coefficient Cc is low, the inclinations of the Lissajous figures greatly differ from each other due to the difference in the oxygen saturation between the inflow phase and the outflow phase of a blood flow. As illustrated in FIG. 8G, when the correlation coefficient Cc is high, since the difference in the oxygen saturation between the inflow phase and the outflow phase of a blood flow is small, the inclinations of the Lissajous figures do not greatly differ from each other.

The transit time calculation unit 253 is configured to calculate the time period from when the correlation coefficient Cc reduces to when the correlation coefficient Cc returns to the original value as the transit time Tt. For example, as illustrated in FIG. 8C, a predetermined threshold th is set as appropriate. The transit time calculation unit 253 may be configured to determine the time period in which the correlation coefficient Cc is lower than the threshold th to be the transit time Tt. The transit time Tt may be determined based on an appropriate rule concerning the Lissajous waveforms illustrated in FIGS. 8E and 8G.

The period in which the correlation coefficient acquisition unit 231 obtains the correlation coefficient Cc is not limited to one signal cycle corresponding to the cardiac cycle of the subject. The cycle may be determined arbitrarily as long as the cycle is sufficiently shorter (for example, 1 second) than the transit time.

In this example, the arterial blood oxygen saturation is changed by causing the subject to stop the breath. However, the arterial blood oxygen saturation may be changed using a combination of the air circuit 111 and the oxygen concentration adjusting unit 112 described with reference to the measurement system 201 according to the second embodiment or a combination of the cuff 113 and the pressure control unit 114.

In the structure according to the embodiment, it is possible to measure the transit time Tt of blood in the biological tissue 2 of the subject using the principle of a pulse photometer without the need to administer an indicator to a blood flow. In addition, the transit time Tt can be calculated by simple processing that acquires the correlation coefficient between the first signal S1 and the second signal S2. Accordingly, biological information of the subject can be measured more easily using the principle of a pulse photometer.

Figure 9A:
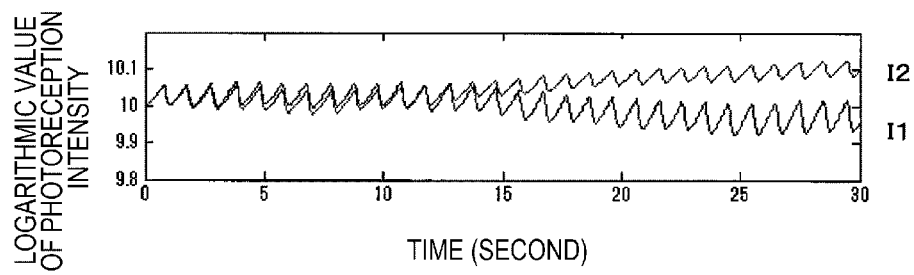
FIGS. 9A-C illustrate a process performed by the biological information measurement system in FIG. 7.
Figure 9B:
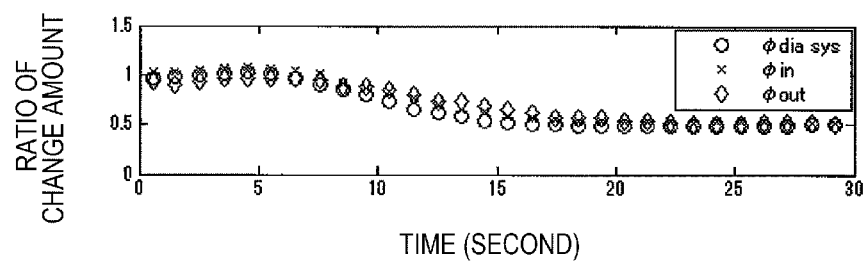

FIG. 9A illustrates the time-dependent change of the logarithmic value of the intensity I1 of the first light and the logarithmic value of the intensity I2 of the second light in the case in which the light emitting unit 10 and the photoreception unit 20 are attached to the fingertip of the subject, the subject is made to raise the hand and hold the breath, and made to resume breathing after a predetermined time. In this case, 940 nm is selected as the first wavelength λ1 and 660 nm is selected as the second wavelength λ2. FIG. 9B illustrates the time-dependent change of the first change amount ratio $\Phi_{in}$ and the second change amount ratio $\Phi_{out}$ measured by the measurement system 201 according to the second embodiment in this case.

Figure 9C:
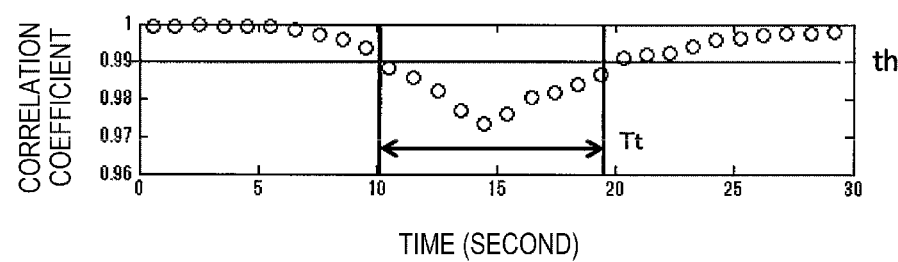

FIG. 9C illustrates the time-dependent change of the correlation coefficient between the time-dependent change waveform for the intensity I1 and the time-dependent change waveform for the intensity I2 illustrated in FIG. 9A. In this example, as FIG. 9B illustrates, there is no significant difference between the time-dependent change of the first change amount ratio $\Phi_{in}$ and the time-dependent change of the second change amount ratio $\Phi_{out}$. However, if the correlation coefficient between the time-dependent change waveform for the intensity I1 and the time-dependent change waveform for the intensity I2 is obtained, the difference between the time-dependent change waveform for the intensity I1 and the time-dependent change waveform for the intensity I2 can be easily recognized. Accordingly, in the structure of the present embodiment, even when it is difficult to recognize significant difference between the time-dependent change of the first change amount ratio $\Phi_{in}$ and the time-dependent change of the second change amount ratio $\Phi_{out}$, the transit time Tt can be calculated easily.

In the measurement system 201, the functions of the correlation coefficient acquisition unit 231 and the transit time calculation unit 253 are provided by software executed by a combination of a processor and a memory interconnected communicably. Examples of the processor include a CPU and MPU. Examples of the memory include a RAM and ROM. However, at least one of the functions of the correlation coefficient acquisition unit 231 and the transit time calculation unit 253 may be provided by hardware such as circuit devices or a combination of hardware and software.

The above embodiments are only examples that facilitate the understanding of the invention. The structures according to the above embodiments may be changed or modified as appropriate without departing from the spirit of the invention. In addition, it will be appreciated that equivalents fall within the technical range of the invention.

What is claimed is:

1. A biological information measurement system comprising:
a light emitting unit configured to emit first light having a first wavelength and second light having a second wavelength;
a photoreception unit configured to output a first signal and a second signal depending on photoreception intensity of the first light and photoreception intensity of the second light that has passed through biological tissue of a subject or that is reflected by the biological tissue of the subject;
a processing period setting unit configured to extract a signal cycle corresponding to a cardiac cycle of the subject for one of the first signal and the second signal, and further configured to set a first processing period in one of a first period in which an effect of arterial blood flowing to the biological tissue is dominant and a second period in which an effect of venous blood flowing from the biological tissue is dominant in the signal cycle;
a first change amount acquisition unit configured to obtain a first change amount corresponding to an attenuation change amount of the first light based on the first signal in the first processing period;
a second change amount acquisition unit configured to obtain a second change amount corresponding to an attenuation change amount of the second light based on the second signal in the first processing period;
a first concentration calculation unit configured to calculate a first concentration of a light absorbing substance in blood of the subject based on the first change amount and the second change amount; and
an output unit configured to provide the first concentration.

2. The biological information measurement system according to claim 1, further comprising:
a differential signal acquisition unit configured to obtain a differential signal by differentiating the one of the first signal and the second signal,
wherein the processing period setting unit is configured to set the first processing period in the first period based on a minimum value of the differential signal.

3. The biological information measurement system according to claim 1, further comprising:
a differential signal acquisition unit configured to obtain a differential signal by differentiating the one of the first signal and the second signal,
wherein the processing period setting unit is configured to set the first processing period in the second period based on a maximum value of the differential signal.

4. The biological information measurement system according to claim 1,
wherein the light absorbing substance is oxyhemoglobin or deoxyhemoglobin.

5. The biological information measurement system according to claim 1,
wherein the light absorbing substance is a dye.

6. The biological information measurement system according to claim 1, wherein the one of the first signal and the second signal is the first signal,
wherein the one of the first period and the second period is the first period,
wherein the processing period setting unit is further configured to extract the signal cycle corresponding to the cardiac cycle of the subject for the second signal, and further configured to set a second processing period in the second period,
wherein the biological information measurement system further comprises:
a third change amount acquisition unit configured to obtain a third change amount corresponding to an attenuation change amount of the first light in the second processing period based on the first signal in the second processing period;
a fourth change amount acquisition unit configured to obtain a fourth change amount corresponding to an attenuation change amount of the second light in the second processing period based on the second signal in the second processing period;
a second concentration calculation unit configured to calculate a second concentration corresponding to the concentration of the light absorbing substance in blood of the subject in the second processing period based on the third change amount and the fourth change amount; and
a transit time calculation unit configured to calculate a transit time of blood in the biological tissue based on the first concentration and the second concentration, and
wherein the output unit is further configured to provide at least one of the first concentration, the second concentration, and the transit time.

7. The biological information measurement system according to claim 6,
wherein the transit time calculation unit is configured to calculate the transit time based on a time difference between a time when the first concentration becomes the maximum and a time when the second concentration becomes the maximum.

8. The biological information measurement system according to claim 6,
wherein the transit time calculation unit is configured to calculate the transit time based on a time difference between a time when the first concentration exceeds a threshold and a time when the second concentration exceeds the threshold.

9. The biological information measurement system according to claim 6,
wherein the transit time calculation unit is configured to calculate the transit time based on a difference between a first mean transit time acquired based on time-dependent change of the first concentration and a second mean transit time acquired based on time-dependent change of the second concentration.

10. The biological information measurement system according to claim 6,
wherein the transit time calculation unit is configured to calculate the transit time based on a cross correlation function between the first concentration and the second concentration.

11. The biological information measurement system according to claim 1, further comprising:
an air circuit configured to supply air to be inhaled by the subject; and
an oxygen concentration adjusting unit configured to adjust a concentration of oxygen included in the air.

12. The biological information measurement system according to claim 1, further comprising:
a cuff attachable to the subject configured to press a blood flow upstream side of the biological tissue.

13. The biological information measurement system according to claim 6, further comprising:
a notifying unit configured to notify when the transit time is outside a predetermined range.

14. A biological information measurement system comprising:
a light emitting unit configured to emit first light having a first wavelength and second light having a second wavelength;
a photoreception unit configured to output a first signal and a second signal depending on photoreception intensity of the first light and photoreception intensity of the second light that has passed through biological tissue of a subject or that is reflected by the biological tissue of the subject;
a processing period set unit configured to extract a signal cycle corresponding to a cardiac cycle of the subject for one of the first signal and the second signal, and further configured to set a first processing period in one of a first period in which an effect of arterial blood flowing to the biological tissue is dominant and a second period in which an effect of venous blood flowing from the biological tissue is dominant in the signal cycle;
a correlation coefficient acquisition unit configured to obtain a correlation coefficient between the first signal and the second signal;
a transit time calculation unit configured to calculate a transit time of blood in the biological tissue based on time-dependent change of the correlation coefficient; and
an output unit configured to provide the transit time.

15. The biological information measurement system according to claim 14, further comprising:
a notifying unit configured to notify when the transit time is outside a predetermined range.

16. A method of measuring biological information, comprising:
emitting first light having a first wavelength and second light having a second wavelength;
outputting a first signal and a second signal depending on photoreception intensity of the first light and photoreception intensity of the second light that has passed through biological tissue of a subject or that is reflected by the biological tissue of the subject;
extracting a signal cycle corresponding to a cardiac cycle of the subject for one of the first signal and the second signal;
setting a first processing period in one of a first period in which an effect of arterial blood flowing to the biological tissue is dominant and a second period in which an effect of venous blood flowing from the biological tissue is dominant in the signal cycle;
obtaining a first change amount corresponding to an attenuation change amount of the first light based on the first signal in the first processing period;
obtaining a second change amount corresponding to an attenuation change amount of the second light based on the second signal in the first processing period;
calculating a first concentration of a light absorbing substance in blood of the subject based on the first change amount and the second change amount; and
providing a calculated result.

17. The method of claim 16, further comprising:
obtaining a differential signal by differentiating the one of the first signal and the second signal; and
setting the first processing period in the first period based on a minimum value of the differential signal.

18. The method of claim 16, further comprising:
obtaining a differential signal by differentiating the one of the first signal and the second signal; and
setting the first processing period in the second period based on a maximum value of the differential signal.

19. The method of claim 16, wherein the one of the first signal and the second signal is the first signal,
wherein the one of the first period and the second period is the first period,
wherein the method further comprises:
extracting the signal cycle corresponding to the cardiac cycle of the subject for the second signal;
setting a second processing period in the second period;
obtaining a third change amount corresponding to an attenuation change amount of the first light in the second processing period based on the first signal in the second processing period;
obtaining a fourth change amount corresponding to an attenuation change amount of the second light in the second processing period based on the second signal in the second processing period;
calculating a second concentration corresponding to the concentration of the light absorbing substance in blood of the subject in the second processing period based on the third change amount and the fourth change amount; and
calculating a transit time of blood in the biological tissue based on the first concentration and the second concentration.

20. The method of claim 16, further comprising:
obtaining a correlation coefficient between the first signal and the second signal; and
calculating a transit time of blood in the biological tissue based on time-dependent change of the correlation coefficient.

* * * * *